United States Patent
Schmidt et al.

(10) Patent No.: US 6,365,543 B1
(45) Date of Patent: Apr. 2, 2002

(54) PROCESS FOR THE PRODUCTION OF AN OXIDATION CATALYST ON-LINE

(75) Inventors: Lanny D. Schmidt, Minneapolis, MN (US); Ashish Bodke, San Jose, CA (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/388,218

(22) Filed: Sep. 1, 1999

Related U.S. Application Data

(60) Provisional application No. 60/099,042, filed on Sep. 3, 1998.

(51) Int. Cl.[7] .......................... B01J 23/00; B01J 23/40; B01J 23/58; B01J 23/72; B01J 23/56

(52) U.S. Cl. .................. 502/325; 502/327; 502/328; 502/331; 502/332; 502/337; 502/338; 502/339; 502/20; 502/22

(58) Field of Search ................................ 502/325, 327, 502/328, 331, 332, 337, 338, 339, 20, 22; 501/95.1

(56) References Cited

U.S. PATENT DOCUMENTS

| | | |
|---|---|---|
| 3,308,181 A | 3/1967 | Pitzer |
| 3,584,060 A | 6/1971 | Rausch |
| 3,670,044 A | 6/1972 | Drehman et al. |
| 4,295,817 A | 10/1981 | Caplin et al. |
| 4,551,574 A | 11/1985 | Imai et al. |
| 4,652,687 A | 3/1987 | Imai et al. |
| 4,788,371 A | 11/1988 | Imai et al. |
| 4,844,837 A | 7/1989 | Heck et al. |
| 4,886,926 A | 12/1989 | Dessau et al. |
| 4,886,928 A | 12/1989 | Imai et al. |

(List continued on next page.)

FOREIGN PATENT DOCUMENTS

| | | |
|---|---|---|
| EP | B1-0178853 | 4/1990 |
| WO | WO 90/06282 | 6/1990 |

OTHER PUBLICATIONS

C. Yokoyama, S. S. Bharadwaj, and L. D. Schmidt, "Platinum–Tin and Platinum–Copper Catalysts for Autothermal Oxidative Dehydrogenation of Ethane to Ethylene," Catalysis Letters, 38 (1996), 181–188.

M. Huff and L. D. Schmidt, "Production of Olefins by Oxidative Dehydrogenation of Propane and Butane Over Monoliths at Short Contact Times," Journal of Catalysis, 149 (1994), 127–141.

M. Huff and L. D. Schmidt, "Ethylene Formation by Oxidative Dehydrogenation of Ethane over Monoliths at Very Short Contact Times," Journal of Physical Chemistry, 97 (1993), 11,815–11,822.

C. Yokoyama, S.S. Bharadqaj, and L.D. Schmidt, "Platinum–Tin and Platinum–Copper Catalysts for Autothermal Oxidative Dehydration of Ethane to Ethylene," Catalysis Letters, 38 (1996), 181–188.

Primary Examiner—Steven P. Griffin
Assistant Examiner—Cam N. Nguyen

(57) ABSTRACT

A process and catalyst for the partial oxidation of paraffinic hydrocarbons, such as ethane, propane, naphtha, and natural gas condensates, to olefins, such as ethylene and propylene. The process involves contacting a paraffinic hydrocarbon with oxygen in the presence of a catalyst under autothermal process conditions. The catalyst comprises a Group 8B metal and, optionally, a promoter metal, such as tin or copper, supported on a fiber monolith support, preferably a ceramic fiber mat monolith. In another aspect, the invention is a process of oxidizing a paraffinic hydrocarbon to an olefin under autothermal conditions in the presence of a catalyst comprising a Group 8B metal and, optionally, a promoter metal, the metals being loaded onto the front face of a monolith support. An on-line method of synthesizing and regenerating catalysts for autothermal oxidation processes is also disclosed.

6 Claims, 1 Drawing Sheet

U.S. PATENT DOCUMENTS

| | | |
|---|---|---|
| 4,886,932 A | 12/1989 | Leyshon |
| 4,897,253 A | 1/1990 | Jenkins |
| 4,902,849 A | 2/1990 | McKay et al. |
| 4,940,826 A | 7/1990 | Font Freide et al. |
| 5,073,657 A | 12/1991 | Warren |
| 5,105,052 A | 4/1992 | Font Freide et al. |
| 5,248,251 A | 9/1993 | Dalla Betta et al. |
| 5,258,567 A | 11/1993 | Kerby et al. |
| 5,306,684 A | 4/1994 | Itoh et al. |
| 5,382,741 A | 1/1995 | Astbury et al. |
| 5,436,383 A | 7/1995 | Le Peltier et al. |
| 5,478,528 A | 12/1995 | Golunski et al. |
| 5,511,972 A * | 4/1996 | Dalla Betta et al. ........ 431/170 |
| 5,527,979 A | 6/1996 | Agaskar et al. |
| 5,593,935 A | 1/1997 | Golunski et al. |
| 5,625,111 A | 4/1997 | Astbury et al. |
| 5,633,421 A | 5/1997 | Iezzi et al. |
| 5,639,929 A | 6/1997 | Bharadwaj et al. |
| 5,648,582 A | 7/1997 | Schmidt et al. |
| 5,654,491 A | 8/1997 | Goetsch et al. |
| 5,658,497 A | 8/1997 | Kumar et al. |
| 5,677,260 A | 10/1997 | Dongara et al. |
| 5,723,403 A * | 3/1998 | Durand et al. ............... 502/304 |
| 5,817,596 A | 10/1998 | Akporiaye et al. |
| 5,830,346 A * | 11/1998 | Harandi et al. .............. 208/113 |
| 5,905,180 A * | 5/1999 | Yokoyama et al. ......... 585/658 |
| 5,953,911 A * | 9/1999 | Guth et al. .................... 60/295 |
| 6,013,599 A * | 1/2000 | Manson ...................... 502/340 |
| 6,037,307 A * | 3/2000 | Campell et al. ............. 502/325 |
| 6,072,097 A * | 6/2000 | Yokoyama et al. ......... 585/658 |

\* cited by examiner

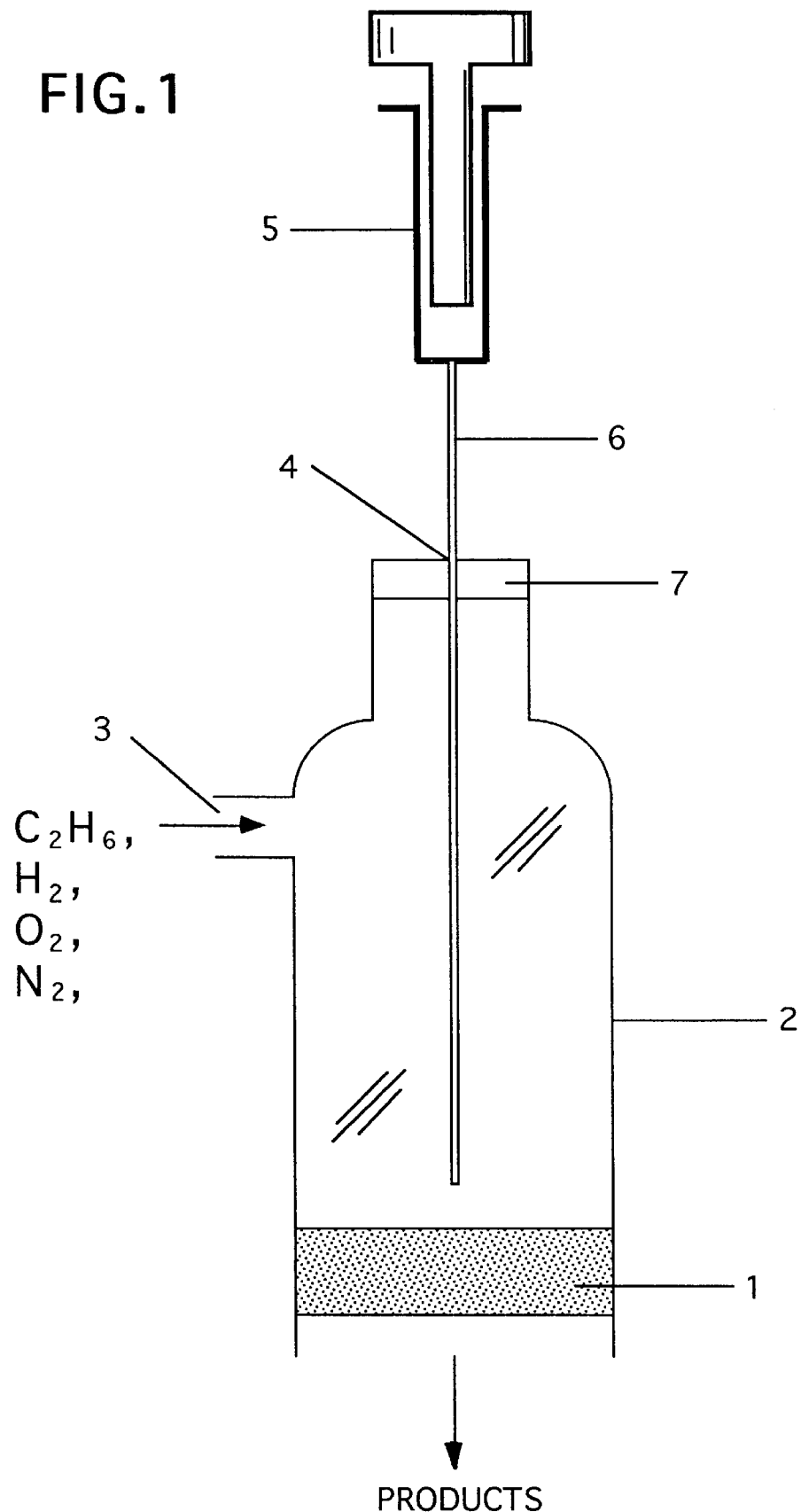

PROCESS FOR THE PRODUCTION OF AN OXIDATION CATALYST ON-LINE

CROSS-REFERENCE TO RELATED APPLICATION

This application claims the benefit of U.S. Provisional Application Ser. No. 60/099,042, filed Sep. 3, 1998.

BACKGROUND OF THE INVENTION

The present invention relates to the field of catalytic oxidation of hydrocarbons. More particularly, the present invention relates to the catalytic partial oxidation of paraffinic hydrocarbons, such as ethane, propane, and naphtha, to produce olefins, such as ethylene and propylene.

Olefins find widespread utility in industrial organic chemistry. Ethylene is needed for the preparation of important polymers, such as polyethylene, vinyl plastics, and ethylene-propylene rubbers, and important basic chemicals, such as ethylene oxide, styrene, acetaldehyde, ethyl acetate, and dichloroethane. Propylene is needed for the preparation of polypropylene plastics, ethylene-propylene rubbers, and important basic chemicals, such as propylene oxide, cumene, and acrolein. Isobutylene is needed for the preparation of methyl tertiary butyl ether. Long chain mono-olefins find utility in the manufacture of linear alkylated benzene sulfonates, which are used in the detergent industry.

Low molecular weight olefins, such as ethylene, propylene, and butylene, are produced almost exclusively by thermal cracking (pyrolysis/steam cracking) of alkanes at elevated temperatures. An ethylene plant, for example, typically achieves an ethylene selectivity of about 85 percent calculated on a carbon atom basis at an ethane conversion of about 60 mole percent. Undesired coproducts are recycled to the shell side of the cracking furnace to be burned, so as to produce the heat necessary for the process. Disadvantageously, thermal cracking processes for olefin production are highly endothermic. Accordingly, these processes require the construction and maintenance of large, capital intensive, and complex cracking furnaces. The heat required to operate these furnaces at a temperature of about 900° C. is frequently obtained from the combustion of methane which disadvantageously produces undesirable quantities of carbon dioxide and nitrogen oxides. As a further disadvantage, the crackers must be shut down periodically to remove coke deposits on the inside of the cracking coils.

Catalytic processes are known wherein paraffinic hydrocarbons are oxidatively dehydrogenated to form mono-olefins. In these processes, a paraffinic hydrocarbon is contacted with oxygen in the presence of a catalyst consisting of a platinum group metal or mixture thereof deposited on a ceramic monolith support in the form of a honeycomb. Optionally, hydrogen may be a component of the feed. The catalyst, prepared using conventional techniques, is uniformly loaded throughout the support. The process can be conducted under autothermal reaction conditions wherein a portion of the feed is combusted, and the heat produced during combustion drives the oxidative dehydrogenation process. Consequently, under autothermal process conditions there is no external heat source required. Representative references disclosing this type of process include the following U.S. Pat. Nos. 4,940,826; 5,105,052; and 5,382,741. A similar process is taught, for example, in U.S. Pat. No. 5,625,111, wherein the ceramic monolith support is in the form of a foam, rather than a honeycomb. Disadvantageously, substantial amounts of deep oxidation products, such as carbon monoxide and carbon dioxide, are produced, and the selectivity to olefins remains too low when compared with thermal cracking. As a further disadvantage, with prolonged use at high temperatures, the ceramic honeycomb and foam monoliths are subject to catastrophic fracture.

C. Yokoyama, S. S. Bharadwaj and L. D. Schmidt disclose in *Catalysis Letters*, 38, 1996, 181–188, the oxidative dehydrogenation of ethane to ethylene under autothermal reaction conditions in the presence of a bimetallic catalyst comprising platinum and a second metal selected from tin, copper, silver, magnesium, cerium, lanthanum, nickel, cobalt, and gold supported on a ceramic foam monolith. The use of a catalyst comprising platinum with tin and/or copper results in an improved olefin selectivity; however, the ceramic foam monolith is still prone to catastrophic fracture.

In view of the above, it would be desirable to discover a catalytic process wherein a paraffinic hydrocarbon is converted to an olefin in a conversion and selectivity comparable to commercial thermal cracking processes. It would be desirable if the catalytic process were to produce small quantities of deep oxidation products, such as carbon monoxide and carbon dioxide. It would also be desirable if the process were to achieve low levels of catalyst coking. It would be even more desirable if the process could be easily engineered without the necessity for a large, capital intensive, and complex cracking furnace. Finally, it would be most desirable if the catalyst was stable and the catalytic support not prone to fracture.

SUMMARY OF THE INVENTION

In one aspect, this invention is a process for the partial oxidation of a paraffinic hydrocarbon to form an olefin. The process comprises contacting a paraffinic hydrocarbon with oxygen in the presence of a catalyst. The contacting is conducted under autothermal process conditions sufficient to form the olefin. The catalyst employed in the process of this invention comprises at least one Group 8B metal supported on a fiber monolith support. Optionally, the catalyst may additionally comprise at least one promoter metal.

The process of this invention efficiently produces olefins, particularly mono-olefins, from paraffinic hydrocarbons and oxygen. In preferred embodiments, the process of this invention achieves a higher paraffin conversion and a higher olefin selectivity as compared with prior art catalytic, autothermal processes. Accordingly, in preferred embodiments, the process of this invention produces fewer undesirable deep oxidation products, such as carbon monoxide and carbon dioxide, as compared with prior art catalytic, autothermal processes. Even more advantageously, in preferred embodiments, the process of this invention achieves a paraffin conversion and olefin selectivity which are comparable to commercial thermal cracking processes. As a further advantage, the process produces little, if any, coke, thereby substantially eliminating problems with coking. Most advantageously, the process of this invention allows the operator to employ a simple engineering design and eliminates the requirement for a large, expensive, and complex furnace, as in thermal cracking processes. More specifically, since the residence time of the reactants in the process of this invention is on the order of milliseconds, the reaction zone used in this process operates at high volumetric throughput. Accordingly, the reaction zone measures from about one-fiftieth to about one-hundredth the size of a commercially available steam cracker of comparable capacity. The reduced size of the reactor reduces costs and greatly simplifies catalyst loading and maintenance procedures. Finally, since the process of this invention is exothermic, the heat produced can be harvested via integrated heat exchangers to produce energy, for example, in the form of steam credits, for other processes.

In another aspect, this invention is a catalyst composition comprising at least one Group 8B metal and at least one promoter metal, said metals being supported on a fiber-monolith support.

The aforementioned composition is beneficially employed as a catalyst in the autothermal partial oxidation of a paraffinic hydrocarbon to an olefin. In preferred embodiments, the catalyst composition beneficially produces the olefin at conversions and selectivities which are comparable to those of industrial thermal cracking processes. As another advantage, the catalyst composition of this invention exhibits good catalyst stability. Additionally, the fiber monolith support which is used in the composition of this invention can be advantageously manufactured into a variety of configurations, such as, without limitation, planar, tubular, and undulating configurations, for specific beneficial results, such as, to maximize the contacting conditions of the reactants with the catalyst and to minimize the pressure drop across the catalyst. As a further advantage, when deactivated the catalyst is easily removed from the reactor and replaced. Most advantageously, the fiber monolith support which is used in the catalyst of this invention is not prone to fracture as are the prior art honeycomb and foam monoliths.

In yet another aspect, this invention is a method of synthesizing or regenerating a catalyst on-line in an autothermal process of oxidizing a paraffinic hydrocarbon to an olefin. For the purposes of this aspect of the invention, the catalyst comprises a Group 8B metal and, optionally, a promoter metal on a monolith support. The term "on-line" means the monolith support, either blank or in the form of a fully deactivated or partially deactivated catalyst, is loaded in the reactor and operating under ignition or autothermal process conditions. A "blank" support is a fresh support absent any Group 8B and, optional, promoter metals. The synthesis/regeneration method comprises contacting the front face of a monolith support with a Group 8B metal compound and/or a promoter metal compound, the contacting being conducted in situ under ignition conditions or autothermal process conditions.

The aforementioned method beneficially allows for the synthesis of an oxidation catalyst on-line under ignition conditions. Additionally, the aforementioned method beneficially allows for the regeneration of a deactivated or partially deactivated oxidation catalyst on-line under autothermal conditions. The method of this invention eliminates the necessity of preparing the catalyst prior to loading a reactor and eliminates the necessity of shutting down the reactor to regenerate or replace the deactivated catalyst. As a further aspect of this invention, novel catalyst compositions can be prepared and screened on-line for catalytic activity. The regeneration process can be beneficially employed on-line to replace metal components of the catalyst which are lost over time through vaporization. Dead sections of the catalyst can be reactivated or regenerated on-line. The aforementioned advantages simplify the handling and maintenance of the catalyst, reduce costs, and improve process efficiency.

The aforementioned on-line method of preparing or regenerating catalysts for autothermal processes produces catalysts in which the active catalytic components are selectively deposited on the front face of the monolith support. Thus, in another aspect, this invention is a catalyst composition comprising at least one Group 8B metal and, optionally, at least one promoter metal, said metal(s) being supported on the front face of a monolith support.

The catalyst composition, described hereinabove, is characterized by front face loading of the Group 8B element(s) and promoter element(s) onto the monolith support. This catalyst can be employed in the partial oxidation of a paraffinic hydrocarbon to an olefin under autothermal process conditions. Catalysts which are front face loaded advantageously exhibit improved activity in these oxidation processes, as compared with catalysts characterized by uniform loading throughout the support.

In yet another aspect, this invention is a second process of partially oxidizing a paraffinic hydrocarbon to an olefin. The process comprises contacting a paraffinic hydrocarbon with oxygen in the presence of a catalyst under autothermal process conditions. The catalyst used herein comprises at least one Group 8B metal and, optionally, at least one promoter metal, said metal(s) being loaded onto the front face of a monolith support.

The aforementioned second autothermal oxidation process employs a catalyst characterized by front face loading of the Group 8B element(s) and optional promoter element(s) onto a monolith support. This second autothermal oxidation process enjoys all of the benefits of the first autothermal oxidation process employing fiber monolith supports, described hereinbefore. More advantageously, the process of this invention characterized by front face loading of the catalyst results in a higher paraffin conversion and a higher olefin selectivity, as compared with catalysts having uniform loading throughout the support.

BRIEF DESCRIPTION OF THE DRAWING

FIG. 1 is an illustration of a reactor which can be used to synthesize or regenerate oxidation catalysts on-line under high temperature conditions, such as the ignition or autothermal conditions of the oxidation process of this invention.

DETAILED DESCRIPTION OF THE INVENTION

The oxidation process of this invention involves the partial oxidation of a paraffinic hydrocarbon to form an olefin. The words "partial oxidation" imply that the paraffin is not substantially oxidized to deep oxidation products, specifically, carbon monoxide and carbon dioxide. Rather, the partial oxidation comprises one or both of oxidative dehydrogenation and cracking to form primarily olefins. It is not known or suggested to what extent or degree either reaction, oxidative dehydrogenation or cracking, predominates or occurs to the exclusion of the other. The process comprises contacting a paraffinic hydrocarbon with oxygen in the presence of a catalyst. The contacting is conducted under autothermal process conditions sufficient to form the olefin. In one aspect, the catalyst which is employed in the process of this invention comprises at least one Group 8B metal and, optionally, at least one promoter metal, said metal(s) being supported on a fiber monolith support. In another aspect, the catalyst employed in the process of this invention comprises at least one Group 8B metal and, optionally, at least one promoter metal, said metal(s) being loaded onto the front face of a monolith support. The term "monolith" refers to a continuous structure, as described in detail hereinafter.

In a preferred embodiment of this invention, the paraffin is selected from ethane, propane, mixtures of ethane and propane, naphtha, gas oils, vacuum gas oils, natural gas condensates, and mixtures of the aforementioned hydrocarbons; and the preferred olefins produced are ethylene, propylene, butene, isobutylene, and butadiene.

In another preferred aspect, the Group 8B metal is a platinum group metal. In a more preferred aspect, the platinum group metal is platinum. The preferred promoter metal is selected from the elements of Groups 2A, 1B, 3A, 4A, (equivalent to Groups 2, 11, 13, 14), and the lanthanide rare earth metals of the Periodic Table of the Elements, as referenced by S. R. Radel and M. H. Navidi, in *Chemistty*, West Publishing Company, New York, 1990. Mixtures of the aforementioned promoter metals can also be employed.

Any paraffinic hydrocarbon or mixture of paraffinic hydrocarbons can be employed in the process of this invention provided that an olefin, preferably, a mono-olefin, is produced. The term "paraffinic hydrocarbon," as used herein, refers to a saturated hydrocarbon. Generally, the paraffinic hydrocarbon contains at least 2 carbon atoms. Preferably, the paraffinic hydrocarbon contains from 2 to about 25 carbon atoms, preferably, from 2 to about 15 carbon atoms, and even more preferably, from 2 to about 10 carbon atoms. The paraffinic hydrocarbon can have a linear, cyclic, or branched structure, and can be a liquid or gas at ambient temperature and pressure. The paraffinic hydrocarbon can be supplied as an essentially pure paraffinic compound or as a paraffin-containing mixture of hydrocarbons. Paraffinic hydrocarbon feeds which are suitably employed in the process of this invention include, but are not limited to, ethane, propane, butane, pentane, hexane, heptane, octane, isomers and higher homologues thereof, as well as complex higher boiling mixtures of paraffin-containing hydrocarbons, such as naphtha, gas oils, vacuum gas oils, and natural gas condensates. Additional feed components may include methane, nitrogen, carbon monoxide, carbon dioxide, and steam, if so desired. Minor amounts of unsaturated hydrocarbons may also be present. Most preferably, the paraffinic hydrocarbon is selected from ethane, propane, mixtures of ethane and propane, naphtha, natural gas condensates, and mixtures of the aforementioned hydrocarbons.

In the process of this invention, the paraffinic hydrocarbon is contacted with an oxygen-containing gas. Preferably, the gas is molecular oxygen or molecular oxygen diluted with an unreactive gas, such as nitrogen, helium, or argon. Any molar ratio of paraffinic hydrocarbon to oxygen is suitable provided the desired olefin is produced in the process of this invention. Preferably, the process is conducted fuel-rich and above the upper flammability limit. A fuel-rich feed reduces the selectivities to deep oxidation products, such as carbon monoxide and carbon dioxide, and beneficially increases the selectivity to olefins. Above the upper flammability limit, homogeneous (gas phase) combustion of the feed is not self-sustaining; therefore, the feed is safer to handle. One skilled in the art would know how to determine the upper flammability limit for different feedstream mixtures comprising the paraffinic hydrocarbon, oxygen, and optionally, hydrogen and a diluent.

Generally, the molar ratio of hydrocarbon to oxygen varies depending upon the specific paraffin feed and process conditions employed. Typically, the molar ratio of paraffinic hydrocarbon to oxygen ranges from about 3 to about 77 times the stoichiometric ratio of hydrocarbon to oxygen for complete combustion to carbon dioxide and water. Preferably, the molar ratio of paraffinic hydrocarbon to oxygen ranges from about 3 to about 13, more preferably, from about 4 to about 11, and most preferably, from about 5 to about 9 times the stoichiometric ratio of hydrocarbon to oxygen for complete combustion to carbon dioxide and water. These general limits are usually achieved by employing a molar ratio of paraffinic hydrocarbon to oxygen greater than about 0.1:1, preferably, greater than about 0.2:1, and by using a molar ratio of paraffinic hydrocarbon to oxygen usually less than about 3.0:1, preferably, less than about 2.7:1. For preferred paraffinic hydrocarbons, the following ratios are more specific. For ethane, the ethane to oxygen molar ratio is typically greater than about 1.5:1, and preferably, greater than about 1.8:1. The ethane to oxygen molar ratio is typically less than about 3.0:1, preferably, less than about 2.7:1. For propane, the propane to oxygen molar ratio is typically greater than about 0.9:1, preferably, greater than about 1.1:1. The propane to oxygen molar ratio is typically less than about 2.2:1, preferably, less than about 2.0:1. For naphtha, the naphtha to oxygen molar ratio is typically greater than about 0.3:1, preferably, greater than about 0.5:1. The naphtha to oxygen molar ratio is typically less than about 1.0:1, preferably, less than about 0.9:1.

Optionally, hydrogen may be co-fed with the paraffinic hydrocarbon and oxygen to the catalyst. The presence of hydrogen in the feedstream beneficially improves the conversion of the paraffinic hydrocarbon and the selectivity to olefins, while reducing the formation of deep oxidation products, such as, carbon monoxide and carbon dioxide. The molar ratio of hydrogen to oxygen can vary over any operable range provided that the desired olefin product is produced. Typically, the molar ratio of hydrogen to oxygen is greater than about 0.5:1, preferably, greater than about 0.7:1, and more preferably, greater-than about 1.5:1. Typically, the molar ratio of hydrogen to oxygen is less than about 3.2:1, preferably, less than about 3.0:1, and more preferably, less than about 2.7:1.

Optionally, the feed may contain a diluent, which can be any gas or vaporizable liquid which is substantially unreactive in the process of the invention. The diluent functions as a carrier of the reactants and products and facilitates the transfer of heat generated by the process. The diluent also helps to minimize undesirable secondary reactions and helps to expand the non-flammable regime for mixtures of the paraffinic hydrocarbon and oxygen, and optionally hydrogen. Suitable diluents include nitrogen, argon, helium, carbon dioxide, steam, and methane. The concentration of diluent in the feed can vary over a wide range. If used, the concentration of diluent is typically greater than about 0.1 mole percent of the total reactant feed including paraffinic hydrocarbon, oxygen, diluent, and optional hydrogen. Preferably, the amount of diluent is greater than about 1 mole percent of the total reactant feed. Typically, the amount of diluent is less than about 70 mole percent, and preferably, less than about 40 mole percent, of the total reactant feed.

In one aspect, the catalyst which is employed in the process of this invention beneficially comprises at least one Group 8B metal, and optionally, at least one promoter metal supported on a fiber monolith support. The Group 8B metals comprise iron, cobalt, nickel, and the platinum group metals, including ruthenium, rhodium, palladium, osmium, iridium, and platinum. Mixtures of the aforementioned Group 8B metals may also be used. Preferably, the Group 8B metal is a platinum group metal; more preferably, the platinum group metal is platinum. The catalyst optionally comprises at least one promoter metal, which is suitably defined as any metal which is capable of enhancing the activity of the catalyst, as measured, for example, by an increase in the paraffinic hydrocarbon conversion, an increase in the selectivity to olefin, a decrease in the formation of deep oxidation products, such as carbon monoxide and carbon dioxide, and/or an increase in catalyst stability and lifetime. Typically, the term "promoter metal" does not include the Group 8B metals. Preferably, the promoter metal is selected from the elements of Groups 2A (for example, Mg, Ca, Sr, Ba), 1B (Cu, Ag, Au), 3A (for example, Al, Ga, In), 4A (for example, Ge, Sn, Pb), the lanthanide rare earth metals, and mixtures thereof. More preferably, the promoter metal is selected from copper, tin and mixtures thereof.

If a promoter metal is employed, then any atomic ratio of Group 8B metal to promoter metal is suitable, provided the catalyst is operable in the process of this invention. The optimal atomic ratio will vary with the specific Group 8B and promoter metals employed. Generally, the atomic ratio of the Group 8B metal to promoter metal is greater than about 0.1 (1:10), preferably, greater than about 0.13 (1:8), and more preferably, greater than about 0.17 (1:6). Generally, the atomic ratio of the Group 8B metal to promoter metal is less than about 2.0 (1:0.5), preferably, less than about 0.33 (1:3), and more preferably, less than about 0.25 (1:4). Compositions prepared with promoter metal alone, in the absence of Group 8B metal, are typically (but not always) catalytically inactive in the process. In contrast, the Group 8B metal is catalytically active in the absence of promoter metal, albeit with lesser activity.

The loading of the Group 8B metal on the fiber support can be any which provides for an operable catalyst in the process of this invention. In general, the loading of the Group 8B metal can be as low as about 0.0001 weight percent, based on the total weight of the Group 8B metal and support. Preferably, the loading of the Group 8B metal is less than about 80 weight percent, preferably, less than about 60 weight percent, and more preferably, less than about 10 weight percent, based on the total weight of the Group 8B metal and the support. Once the platinum loading is established, the desired atomic ratio of Group 8B metal to promoter metal determines the loading of the promoter metal.

In one aspect of this invention, the catalytic support is a fiber monolith. As used herein, the term "monolith" means any continuous structure, preferably, in one piece or unit. As an example, a plurality of fibers can be woven into a cloth or made into non-woven mats or thin paper-like sheets to form a fiber monolith. In another example, one long continuous fiber can be wound upon itself and used as a fiber monolith. Catalysts prepared with fiber monoliths tend to have a higher activity as compared with catalysts prepared with foam monoliths and gauzes. Additionally, fibers possess higher fracture resistance as compared with foam and honeycomb supports of the prior art.

Preferably, the catalytic support is a ceramic fiber monolith. Non-limiting examples of ceramics which are suitable for this invention include refractory oxides and carbides, such as, alumina, silica, silica-aluminas, aluminosilicates, including cordierite, zirconia, titania, boria, zirconia mullite alumina (ZTA), lithium aluminum silicates, and oxide-bonded silicon carbide. Mixtures of the aforementioned refractory oxides and carbides may also be employed. Preferred ceramics include alumina, silica, and amorphous or crystalline combinations of alumina and silica, including mullite. Alpha ($\alpha$) and gamma ($\gamma$) alumina are preferred. Preferred combinations of alumina and silica comprise from about 60 to about 100 weight percent alumina and from essentially zero to about 40 weight percent silica. Other refractory oxides, such as boria, can be present in smaller amounts in the preferred alumina and silica mixtures. Preferred zirconias include zirconia fully stabilized with calcia (SSZ) and zirconia partially stabilized with magnesia (PSZ).

More preferred ceramic fibers, such as those available as Nextel® brand ceramic fibers (a trademark of 3M Corporation), typically have a diameter greater than about 1 micron ($\mu$m), preferably, greater than about 5 microns ($\mu$m). The diameter is suitably less than about 20 $\mu$m, preferably, less than about 15 $\mu$m. The length of the fibers is generally greater than about 0.5 inch (1.25 cm), preferably, greater than about 1 inch (2.5 cm), and typically less than about 10 inches (25.0 cm), preferably, less than about 50 inches (12.5 cm). The surface area of the fibers is very low, being generally less than about 1 m$^2$/g, preferably, less than about 0.3 m$^2$/g, but greater than about 0.001 m$^2$/g. Preferably, the fibers are not woven like cloth, but instead are randomly intertwined as in a non-woven mat or matted rug. Most preferred are Nextel® brand 312 fibers which consist essentially of alumina (62 weight percent), silica (24 weight percent), and boria (14 weight percent). Non-limiting examples of other suitable fibers include Nextel® brand 440 fibers which consist essentially of gamma alumina (70 weight percent), silica (28 weight percent), and boria (2 weight percent) and Nextel® brand 610 fibers which consist essentially of alpha alumina (99 weight percent), silica (0.2–0.3 weight percent) and iron oxide (0.4–0.7 weight percent). Preferably, the fibers are not wash-coated.

The deposition of the Group 8B metal and promoter metal onto the support can be made by any technique known to those skilled in the art, for example, impregnation, ion-exchange, deposition-precipitation, vapor deposition, sputtering, and ion implantation. In one preferred method the Group 8B metal is deposited onto the support by impregnation. Impregnation is described by Charles N. Satterfield in *Heterogeneous Catalysis in Practice*, McGraw-Hill Book Company, New York, 1980, 82–84, incorporated herein by reference. In this procedure, the support is wetted with a solution containing a soluble Group 8B metal compound, preferably, to the point of incipient wetness. The temperature of the deposition typically ranges from about ambient, taken as 23° C., to about 100° C., preferably, from about 23° C. to about 50° C. The deposition is conducted usually at ambient pressure. Non-limiting examples of suitable Group 8B metal compounds include the Group 8B metal nitrates, halides, sulfates, alkoxides, carboxylates, and Group 8B metal organometallic compounds, such as halo, amino, and carbonyl complexes. Preferably, the Group 8B metal compound is a platinum group halide, more preferably, a chloride, such as chloroplatinic acid. The solvent can be any liquid which solubilizes the Group 8B metal compound. Suitable solvents include water, aliphatic alcohols, aliphatic and aromatic hydrocarbons, and halo-substituted aliphatic and aromatic hydrocarbons. The concentration of the Group 8B metal compound in the solution generally ranges from about 0.001 molar (M) to about 10 M. After contacting the support with the solution containing the Group 8B metal compound, the support may be dried under air at a temperature ranging from about 23° C. to a temperature below the decomposition temperature of the Group 8B metal compound, typically, a temperature between about 23° C. and about 100° C.

The deposition of the promoter metal can be accomplished in a manner analogous to the deposition of the Group 8B metal. Accordingly, if impregnation is used, then the support is wetted with a solution containing a soluble promoter metal compound at a temperature between about 23° C. and about 100° C., preferably, between about 23° C. and about 50° C., at about ambient pressure. Suitable examples of soluble promoter metal compounds include promoter metal halides, nitrates, alkoxides, carboxylates, sulfates, and promoter metal organometallic compounds, such as amino, halo, and carbonyl complexes. Suitable solvents comprise water, aliphatic alcohols, aliphatic and aromatic hydrocarbons, and chloro-substituted aliphatic and aromatic hydrocarbons. Certain promoter metal compounds, such as compounds of tin, may be more readily solubilized in the presence of acid, such as hydrochloric acid. The concentration of the promoter metal compound in the solution generally ranges from about 0.01 M to about 10 M. Following deposition of the soluble promoter metal compound or mixture thereof, the impregnated support may be dried under air at a temperature between about 23° C. and a temperature below the temperature wherein vaporization or decomposition of the promoter metal compound occurs. Typically, the drying is conducted at a temperature between about 23° C. and about 100° C.

In one method of preparing the catalyst, the Group 8B metal is deposited onto the support first, and thereafter the promoter metal is deposited onto the support. In an alternative method, the promoter metal is deposited first, followed by the deposition of the Group 8B metal. In a preferred method of preparing the catalyst, the Group 8B metal and the promoter metal are deposited simultaneously onto the support from the same deposition solution.

Following one or more depositions of the Group 8B metal and optional promoter metal onto the support, a calcination under oxygen is optional. If performed, the calcination is conducted at a temperature ranging from about 100° C. to below the temperature at which volatilization of the metals becomes significant, typically, a temperature less than about 1,100° C. Preferably, the calcination is conducted at a temperature between 100° C. and about 500° C.

As a final step in the preparation of the catalyst, the fully loaded support is reduced under a reducing agent, such as hydrogen, carbon monoxide, or ammonia, at a temperature between about 100° C. and about 800° C., preferably between about 125° C. and about 600° C., so as to convert the Group 8B metal substantially to its elemental form. The promoter metal may be reduced fully or partially, or not reduced at all, depending upon the specific promoter metal chosen and the reduction conditions. In addition, reduction at elevated temperatures may produce alloys of the Group 8B metal and the promoter metal. Alloys may provide enhanced catalyst stability by retarding vaporization of the promoter metal during the process of this invention.

In another preferred embodiment, the Group 8B metal(s) and optional promoter metal(s) are loaded onto the front face, that is, the upstream face, of the monolith support, as opposed to being uniformly loaded throughout the support. Front face (or up-front) loading leads to improved selectivity to olefins in the oxidation process of this invention. As a guideline, the term "front face loading" may be interpreted to mean that typically greater than about 65 weight percent, preferably, greater than about 75 weight percent, and more preferably, greater than about 90 weight percent, of the Group 8B metal and optional promoter metal(s), are supported within the front 1/3 of the thickness of the support. Preferably, these amounts of metals are supported within the front 3 mm of the support. If the support is not yet loaded into the reactor, front face loading can be accomplished by conventional techniques, such as, impregnation onto the front face of a blank support with solutions of the platinum and promoter metals. In a more preferred embodiment, the front face-loaded catalyst is prepared on-line, that is, prepared after the support, typically a blank support, is loaded into the reactor, placed under reaction conditions, and contacted with a Group 8B metal compound and, optionally, a promoter metal compound. On-line front face loading facilitates the synthesis and screening of new catalysts without shutting down and reloading the reactor. Regeneration of the catalyst can also be conducted on-line, as noted hereinafter. Advantageously, the on-line front face loading method described herein is generally adaptable to other high temperature catalytic processes.

As noted hereinabove, on-line up-front loading can be accomplished by contacting the front face of the monolith support, typically a blank monolith, with at least one Group 8B metal compound and/or at least one promoter metal compound, the contacting being conducted in situ, that is, in the reactor under process conditions. For this aspect of the invention, the monolith can take any form, including, a foam or honeycomb, a fiber mat, a gauze, or any other regular or irregular, continuous particle or structure. For this aspect of the invention, the term "process conditions" includes ignition and autothermal conditions, described in detail hereinafter. Typically, ignition conditions are used when a catalyst is being synthesized fiom a blank monolith. Typically, autothermal conditions are used when a partially deactivated catalyst is being regenerated. The contacting can be continuous or intermittent, as desired. A preferred method of contacting comprises dripping or spraying a solution containing a soluble compound of the Group 8B metal and/or promoter metal onto the front face of the support. The solution containing the metal components can be, for example, any of the impregnation solutions used in the catalyst preparation described hereinbefore.

In one preferred embodiment, the reactor for achieving on-line synthesis and regeneration comprises the design shown in FIG. 1. In this design, the blank monolith or the catalyst itself (1) is packed into a quartz reactor (2). A radiation shield (not shown in figure) is preferably placed below the monolith or catalyst. A port (3) above the front face of the monolith or catalyst provides an entry for the feedstream containing the paraffinic hydrocarbon, oxygen, and optional diluent and hydrogen. The feedstream passes through the catalyst to the downstream exit port (not shown). Above the front face of the monolith or catalyst a second port (4) provides a means for introducing the Group 8B metal compound and/or promoter metal compound into the reactor. Suitable means, as shown in FIG. 1, can be a hypodermic syringe (5) with a needle (6) passing through a rubber septum (7) into the reactor (2). Other suitable delivery means include pipets, spray nozzles, faucets, and other conventional devices designed for the delivery of solutions into high temperature reactors. The entire reactor (2) can be wrapped in high temperature insulation (not shown in the figure) so as to retard heat losses and maintain adiabatic or near adiabatic conditions.

The process of this invention is required to be conducted under autothermal process conditions. Under these conditions, the heat generated by the combustion of a portion of the feed is sufficient to support the dehydrogenation and/or thermal cracking of the paraffin to the olefin. Accordingly, the need for an external heat source to supply the energy for the process is eliminated. As a requirement for conducting an autothermal process, the catalyst should be capable of combustion beyond the normal fuel rich limit of flammability. The catalyst of this invention possesses this required capability. Ignition can be effected by preheating the feed to a temperature sufficient to effect ignition when contacted with the catalyst. Alternatively, the feed can be ignited with an ignition source, such as a spark or flame. Once ignited, the process runs autothermally such that the exothermic heat of combustion drives the dehydrogenation/cracking process. While running autothermally, the paraffin feed does not have to be preheated, although it can be preheated if desired. Typical preheat temperatures range from about 40° C. to about 400° C.

As a general rule, the autothermal process operates at close to the adiabatic temperature that is, essentially without loss of heat), which is typically greater than about 750° C., and preferably, greater than about 925° C. Typically, the autothermal process operates at a temperature less than about 1,150° C., and preferably, less than about 1,050° C. Pressures range typically from about 1 atmosphere absolute (atm abs) (100 kPa abs) to about 20 atm abs (2,000 kPa abs), preferably, from about 1 atm abs (100 kPa abs) to about 10 atm (1,000 kPa abs), and more preferably, from about 1 atm abs (1,000 kPa abs) to about 7 atm abs (700 kPa abs).

It is beneficial to maintain a high space velocity through the reaction zone, otherwise the selectivity to olefinic products may decrease due to undesirable side reactions. Generally, the gas hourly space velocity (GHSV), calculated as the total flow of the hydrocarbon, oxygen, optional hydrogen, and optional diluent flows, is greater than about 50,000 ml total feed per ml catalyst per hour ($h^{-1}$) measured at standard temperature and pressure (0° C., 1 atm). Preferably, the GHSV is greater than about 80,000 $h^{-1}$, and more preferably, greater than 100,000 $h^{-1}$. Generally, the gas hourly space velocity is less than about 6,000,000 $h^{-1}$, preferably, less than about 4,000,000 $h^{-1}$, more preferably, less than 3,000,000 $h^{-1}$, measured as the total flow at standard temperature and pressure. Gas flows are typically monitored in units of liters per minute at standard temperature and pressure (slpm). The conversion of gas flow from "slpm" units to gas hourly space verity units ($h^{-1}$) is made as follows:

$$GHSV\ h^{-1} = \frac{slpm \times 1000\ cm^3/min \times 60\ min/h}{\text{cross-sectional area of catalyst}\ (cm^2) \times \text{length}\ (cm)}$$

When a paraffinic hydrocarbon is contacted with oxygen under autothermal process conditions in the presence of the catalyst described hereinabove, an olefin, preferably a mono-olefin, is produced. Ethane is converted primarily to ethylene. Propane and butane are converted primarily to ethylene and propylene. Isobutane is converted primarily to isobutylene and propylene. Naphtha and other higher molecular weight paraffins are converted primarily to ethylene and propylene.

The conversion of paraffinic hydrocarbon in the process of this invention can vary depending upon the specific feed composition, catalyst, and process conditions employed. For the purposes of this invention, "conversion" is defined as the mole percentage of paraffinic hydrocarbon in the feed which is converted to products. Generally, at constant pressure and space velocity, the conversion increases with increasing temperature. Typically, at constant temperature and pressure, the conversion does not change significantly over a wide range of high space velocities employed. In this process, the conversion of paraffinic hydrocarbon is typically greater than about 45 mole percent, preferably, greater than about 55 mole percent, and more preferably, greater than about 60 mole percent.

Likewise, the selectivity to products will vary depending upon the specific feed composition, catalyst, and process conditions employed. For the purposes of this invention, "selectivity" is defined as the percentage of carbon atoms in the converted paraffin feed which react to form a specific product. For example, the olefin selectivity is calculated as follows:

Moles of olefin formed×Number of carbon atoms in olefin×100
Moles of paraffin converted×Number of carbon atoms in paraffin Generally, the olefin selectivity increases with increasing temperature up to a maximum value and declines as the temperature continues to rise. Usually, the olefin selectivity does not change substantially over a wide range of high space velocities employed. In the process of this invention, the olefin selectivity, preferably, the combined selectivity to ethylene and propylene, is typically greater than about 60 carbon atom percent, preferably, greater than about 70 carbon atom percent, and more preferably, greater than about 80 carbon atom percent. Other products formed in smaller quantities include methane, carbon monoxide, carbon dioxide, propane, butenes, butadiene, propadiene, acetylene, methylacetylene, and $C_{6+}$ hydrocarbons. Acetylene can be hydrogenated downstream to increase the overall selectivity to olefin. Carbon monoxide, carbon dioxide, and methane may be recycled, at least in part, to the reactor.

Water is also formed in the process of this invention from the combustion of hydrogen or hydrocarbon. Preferably, water is formed by the combustion of hydrogen. Accordingly, it is advantageous to recycle the hydrogen in the product stream, obtained from the oxidative dehydrogenation of the paraffinic hydrocarbon, back to the reactor. The presence of hydrogen in the feed minimizes the formation of carbon oxides by reacting with the oxygen to produce water and energy. Optimally, the hydrogen needed to meet the demands of the process essentially equals the hydrogen formed during conversion of the paraffinic hydrocarbon to olefin. Under these balanced conditions, the hydrogen forms a closed loop wherein there is essentially no demand for additional hydrogen to be added to the fuel.

Over time the catalyst may lose activity due to the loss of catalytic components by vaporization. It has now been discovered that the catalyst can be easily regenerated on-line during the autothermal oxidation process. With this regeneration method, there is no need to shut down the process and remove the catalyst from the reactor. Rather, the regeneration comprises contacting the front face of the partially deactivated or fully deactivated catalyst with a Group 8B metal compound and/or a promoter metal compound in situ during operation under autothermal process conditions. Typically, the front face of the catalyst is contacted with a solution containing the Group 8B metal compound and/or promoter metal compound. Details of the equipment and contacting methods have been described hereinbefore for front face on-line loading of the monolith.

The invention will be further clarified by a consideration of the following examples, which are intended to be purely illustrative of the use of the invention. Other embodiments of the invention will be apparent to those skilled in the art from a consideration of this specification or practice of the invention as disclosed herein. Unless otherwise noted, all percentages are given on a mole percent basis. Selectivities are given on a carbon atom percent basis.

EXAMPLE 1 (E-1)

Autothermal Oxidation of Ethane to Ethylene over Pt—Sn on Fiber Monolith

A catalyst comprising platinum and tin in a Pt:Sn atomic ratio 1:7 on a fiber mat was prepared as follows. A non-woven fiber monolith (3M Corporation, Nextel® brand 312, non-woven pressed fiber mat; outer dimensions, 18 mm diameter by 2 mm thick; filament diameter, 10–12 microns) was impregnated to incipient wetness with an aqueous solution of hydrogen hexachloroplatinate (0.075 g in 7.5 ml water) and then air dried overnight. The dried monolith was calcined in air at 100° C. for 1 h and then at 600° C. for 2 h. The platinum loading, determined by difference in weights, was found to be 2 weight percent. The monolith was further impregnated with an aqueous solution of stannous chloride (0.05 g in 7.5 ml water) containing 2 drops of hydrochloric acid to assist in the dissolution of the salt. Sufficient tin solution was used to give a Pt:Sn atomic ratio of 1:7. After drying in air overnight, the impregnated monolith was calcined in air at 100° C. for 1 h and at 700° C. for 2 h.

The catalyst was packed between blank alumina foam monoliths (outer diameter 18 mm by 10 mm length; 45 pores per linear inch) and inserted into a quartz reactor. A mixture of ethane, hydrogen, nitrogen, and oxygen was fed to the reactor. The gas mixture was heated indirectly by holding a Bunsen burner flame to the outside of the reactor until the catalyst lit off. Once the catalyst was ignited, the Bunsen burner was removed and the process was run autothermally. The reactor was radially insulated to maintain adiabatic and autothermal operation. Pressure was 1.34 atm abs. Autothermal temperature was typically between 800° C. and 1,100° C. Process conditions and results are summarized in Table 1.

TABLE 1

Autothermal Oxidation of Ethane to Ethylene[a]
Catalyst: 2% Pt on Non-Woven Fiber Mat (Sn/Pt = 7:1)

| Total Flow Rate, slpm | $C_2H_6/O_2$ Molar Ratio | $H_2/O_2$ Molar Ratio | % $N_2$ | % $C_2H_6$ Conv | % Selectivity: | | | | | |
|---|---|---|---|---|---|---|---|---|---|---|
| | | | | | $C_2H_4$ | CO | $CO_2$ | $CH_4$ | $C_2H_2$ | $C_{3,4}$ |
| 5.0 | 2 | 0 | 30 | 69.2 | 69.8 | 14.7 | 6.9 | 4.6 | 0.5 | 3.5 |
| 7.5 | 2 | 2 | 20 | 68.2 | 84.0 | 5.5 | 0.5 | 5.7 | 0.2 | 4.1 |

[a]Pressure = 1.34 atm abs.

It was seen that a catalyst comprising platinum and tin deposited on a ceramic fiber mat support was capable of oxidizing ethane to ethylene in the presence of oxygen and hydrogen under autothermal conditions. Ethane conversion was between 68 and 69 percent; ethylene selectivity reached a high of 84.0 percent. Carbon monoxide was lowest at 5.5 percent.

Comparative Experiment 1 (CE-1)—Autothermal Oxidation of Ethane to Ethylene Over Pt—Sn on Foam Monolith An alumina foam monolith (outer diameter 18 mm by 10 mm length; 45 pores per linear inch) was impregnated to incipient wetness with an aqueous solution of hydrogen hexachloroplatinate (0.3 g in 2.5 ml water) and dried overnight under ambient conditions. The dried monolith was calcined in air at 100° C. for 1 h and then at 600° C. for 2 h. The platinum loading was 2 weight percent. The monolith was further impregnated with an aqueous solution of stannous chloride (1.8 g in 2.5 ml water) acidified with 4 drops of hydrochloric acid to assist in the dissolution of the salt. After drying overnight, the monolith was calcined in air at 100° C. for 1 h and at 700° C. for 2 h. The Sn:Pt atomic ratio was 7:1. The catalyst was packed into a quartz reactor as in E-1. A feed stream comprising ethane, hydrogen, nitrogen, and oxygen was fed through the catalyst; the catalyst was ignited; and the process was run autothermally in the manner described in E-1. Results are shown in Table 2.

It was seen that a catalyst comprising platinum and tin on an alumina foam monolith was capable of oxidizing ethane to ethylene in the presence of hydrogen and oxygen under autothermal conditions. Ethane conversion was between 68 and 69 percent; ethylene selectivity reached a high of 84.1 percent. When E-1 was compared with CE-1 under similar process conditions, it was seen that the process using the catalyst prepared on a fiber monolith was comparable to the process with the catalyst prepared on a foam monolith.

Whereas the foam monolith is prone to fracture under long-term use, the fiber support advantageously is not prone to fracture.

Comparative Experiment 2 (CE-2)

Autothermal Oxidation of Ethane to Ethylene Over Pt Gauze Coated with Tin

Three gauzes (Alfa Aesar) composed of pure platinum (99.9 weight percent metals basis) woven from platinum wires (0.0762 mm wire diameter; 100 mesh (149 microns); 18 mm, external gauze diameter) were coated on both sides with metallic tin to a thickness of 3000 Å by use of metal evaporation techniques. The three gauzes were packed together between two blank alumina foam monoliths (outer diameter 18 mm by 10 mm length; 45 pores per linear inch), and inserted into a quartz reactor. A mixture of ethane, hydrogen, nitrogen, and oxygen was passed through the reactor; the catalyst was lit, and the process was run autothermally as described in E-1 hereinabove. Process conditions and results are shown in Table 3.

TABLE 2

Autothermal Oxidation of Ethane to Ethylene[a]
Catalyst: 2% Pt on Alumina Foam Monolith (Sn/Pt = 7:1)

| Total Flow Rate, slpm | $C_2H_6/O_2$ Molar Ratio | $H_2/O_2$ Molar Ratio | % $N_2$ | % Conv $C_2H_6$ | % Selectivity: | | | | | |
|---|---|---|---|---|---|---|---|---|---|---|
| | | | | | $C_2H_4$ | CO | $CO_2$ | $CH_4$ | $C_2H_2$ | $C_{3,4}$ |
| 5.0 | 2 | 0 | 30 | 68.8 | 69.7 | 15.4 | 6.9 | 4.2 | 0.2 | 3.6 |
| 7.5 | 2 | 2 | 20 | 67.6 | 84.1 | 5.2 | 0.3 | 5.2 | 1.3 | 3.9 |

[a]Pressure = 1.34 atm abs.

TABLE 3

Autothermal Oxidation of Ethane to Ethylene[a]
Catalyst: 100 Mesh Platinum Gauze (3000 Å Sn)

| Total Flow Rate, slpm | $C_2H_6/O_2$ Molar Ratio | $H_2/O_2$ Molar Ratio | % $N_2$ | % Conv | % Selectivity: | | | | | |
|---|---|---|---|---|---|---|---|---|---|---|
| | | | | | $C_2H_6$ | $C_2H_4$ | CO | $CO_2$ | $CH_4$ | $C_2H_2$ | $C_{3,4}$ |
| 7.5 | 2 | 2 | 20 | 62.2 | 81.1 | 6.6 | 0.4 | 4.5 | 3.3 | 4.1 |

[a]Pressure = 1.34 atm abs.

It was seen that a catalyst comprising platinum gauze coated with tin was capable of oxidizing ethane to ethylene in the presence of oxygen and hydrogen under autothermal conditions. Ethane conversion was 62.2 percent; ethylene selectivity was 81.1 percent. Carbon monoxide selectivity was 6.6 percent. When E-1 was compared with CE-2 under identical process conditions, it was seen that the catalyst prepared on the fiber monolith achieved a higher conversion, a higher ethylene selectivity, and a lower carbon monoxide selectivity than the catalyst prepared on the gauze.

EXAMPLE 2 (E-2)
Catalyst Regeneration: On-Line Sn Addition to Catalyst

A platinum-tin catalyst was prepared on a non-woven fiber mat monolith as described in E-1 hereinabove. The platinum loading was 2 weight percent, and the Sn:Pt atomic ratio was 7:1. The catalyst was packed between two blank foam alumina monoliths (outer diameter 18 mm by 10 mm length; 45 pores per linear inch) in a quartz reactor. A mixture of ethane, hydrogen, nitrogen, and oxygen was fed through the reactor under the process conditions shown in Table 4. Light-off of the catalyst and autothermal operation were as described in E-1 hereinabove. The selectivity and conversion were monitored at 1.5 and 20 h of continuous operation, as shown in Table 4.

drop of hydrochloric acid to assist solubility. This solution (0.4 ml) was dripped uniformly onto the front surface of the partially deactivated catalyst while the apparatus was in use under autothermal conditions. The apparatus used for the on-line regeneration was similar to that shown in FIG. 1. Results of the on-line regeneration are found in Table 4. It was found that the on-line addition of tin to the partially deactivated catalyst regenerated the catalyst restoring both ethane conversion and ethylene selectivity to near initial levels.

EXAMPLE 3 (E-3)
On-Line Catalyst Preparation: Front Face Loading

Two blank alumina foam monoliths (outer diameter 18 mm by 10 mm length; 45 pores per linear inch) were packed into a quartz reactor, and a mixture of ethane, hydrogen, nitrogen, and oxygen was passed through the reactor. The total feed flow rate was maintained at 7.5 slpm; nitrogen dilution was 20 percent; and the ethane/oxygen and hydrogen/oxygen molar ratios were both maintained at 2/1. The monoliths were heated using a Bunsen burner flame, but they failed to light off. Hydrogen hexachloroplatinate (0.04 g) was dissolved in distilled water (5 ml). A portion of this solution was sucked into a syringe (1 cc), and the solution (0.4 ml) was uniformly dripped onto the front surface of the front alumina monolith under ignition conditions (external heat from Bunsen burner). The apparatus for delivering the

TABLE 4

On-Line Regeneration of Pt-Sn Catalyst[a]

| Time on line h | Total Flow Rate, slpm | $C_2H_6/O_2$ Molar Ratio | $H_2/O_2$ Molar Ratio | % $N_2$ | % Conv $C_2H_6$ | % Selectivity: | | | | | |
|---|---|---|---|---|---|---|---|---|---|---|---|
| | | | | | | $C_2H_4$ | CO | $CO_2$ | $CH_4$ | $C_2H_2$ | $C_{3,4}$ |
| 1.5 | 7.5 | 2 | 2 | 20 | 68.2 | 84.0 | 5.5 | 0.5 | 5.7 | 0.2 | 4.1 |
| 20.0 | 7.5 | 2 | 2 | 20 | 60.4 | 81.0 | 7.4 | 0.9 | 5.6 | 0.0 | 5.1 |
| After Regen. | 7.5 | 2 | 2 | 20 | 66.1 | 83.2 | 5.8 | 0.4 | 5.4 | 0.9 | 4.3 |

[a]Pressure = 1.34 atm abs.

It was found that the ethane conversion and ethylene selectivity decreased with time. At 20 h of continuous use the partially deactivated catalyst was regenerated using the following on-line regeneration technique. Stannous chloride (0.1 g) was dissolved in distilled water (8 ml) containing 1 solution was similar to that shown in FIG. 1. The solution was observed to dry quickly under the influence of external heating and changed color from yellow to black, before the catalyst lit off. Results using this front face loaded catalyst, which was prepared on-line, are given in Table 5 (first row).

TABLE 5

On-Line Catalyst Preparation[a]

| Catalyst | Total Flow Rate, slpm | $C_2H_6/O_2$ Molar Ratio | $H_2/O_2$ Molar Ratio | % Conv | % Selectivity: | | | | | | |
|---|---|---|---|---|---|---|---|---|---|---|---|
| | | | | | $N_2$ | $C_2H_6$ | $C_2H_4$ | CO | $CO_2$ | $CH_4$ | $C_2H_2$ | $C_{3,4}$ |
| Pt | 7.5 | 2 | 2 | 20 | 60.5 | 81.1 | 9.1 | 0.5 | 4.5 | 0.4 | 4.4 |
| Pt—Sn | 7.5 | 2 | 2 | 20 | 65.2 | 84.4 | 5.2 | 0.3 | 5.0 | 1.2 | 3.9 |
| Pt—Sn—Cu | 7.5 | 2 | 2 | 20 | 64.3 | 84.6 | 5.6 | 0.6 | 4.7 | 0.9 | 3.6 |

[a]Pressure = 1.34 atm abs.

After the platinum solution was dripped onto the blank monolith and lit off, the syringe was replaced by a second syringe containing an aqueous solution of tin chloride (0.15 g in 5 ml distilled water). Approximately 0.4 ml of this solution was dripped uniformly under autothermal conditions over the front face of the platinum catalyst to prepare a platinum-tin catalyst in situ. Results using this catalyst are shown in Table 5 (second row). It was found that the on-line addition of tin to the front face of platinum catalyst produced a Pt—Sn catalyst with improved ethane conversion and improved ethylene selectivity. Also, carbon monoxide and carbon dioxide production were significantly reduced. Thereafter, the syringe was replaced by a third syringe containing an aqueous solution of copper nitrate (0.15 g in 5 ml distilled water). Approximately 0.4 ml of this solution was dripped uniformly over the front face of the platinum-tin catalyst under autothermal conditions to prepare a platinum-tin-copper catalyst in situ. Results are shown in Table 5 (third row). It was found that the on-line addition of copper to the front face of the platinum-tin catalyst produced a Pt—Sn—Cu catalyst which improved performance when compared with the pure platinum catalyst.

Comparative Experiment 3 (CE-3)—Uniform Catalyst Loading

An alumina monolith (outer diameter 18 mm by 100 mm length; 45 pores per linear inch) was uniformly loaded by impregnation to incipient wetness with an aqueous solution (2 ml) of hydrogen hexachloroplatinate and then dried overnight under ambient conditions. The dried monolith was calcined in air at 100° C. for 1 h and then at 600° C. for 2 h. The platinum loading was 5 weight percent. The platinum catalyst was packed between blank alumina monoliths and inserted into the center of a quartz reactor, in a manner similar to E-1 hereinabove. A mixture of ethane, hydrogen, nitrogen, and oxygen was passed through the reactor and ignited as in Example 1. After light off, the process was run autothermally as in Example 1, with the process conditions and results shown in Table 6.

TABLE 6

Ethane Oxidation to Ethylene[a]
Catalyst: 5% Pt on Alumina Foam Monolith

| Total Flow Rate, slpm | $C_2H_6/O_2$ Molar Ratio | $H_2/O_2$ Molar Ratio | % Conv | % Selectivity: | | | | | | |
|---|---|---|---|---|---|---|---|---|---|---|
| | | | | $N_2$ | $C_2H_6$ | $C_2H_4$ | CO | $CO_2$ | $CH_4$ | $C_2H_2$ | $C_{3,4}$ |
| 5.0 | 2 | 0 | 30 | 62.5 | 61.5 | 23.8 | 6.6 | 3.5 | 0.2 | 4.4 |
| 7.5 | 2 | 2 | 20 | 63.9 | 74.6 | 12.8 | 0.9 | 6.0 | 0.3 | 5.4 |

[a]Pressure = 1.34 atm abs.

When CE-3 (Table 6, second row) was compared with E-3 under identical process conditions (Table 5, first row), it was found that the platinum catalyst which was loaded on-line onto the front face of the monolith advantageously achieved a higher ethylene selectivity and lower carbon monoxide and carbon dioxide selectivities, as compared with the comparative platinum catalyst which was uniformly loaded.

What is claimed is:

1. A process of synthesizing or regenerating an oxidation catalyst on-line, the catalyst comprising at least one Group 8B metal and, optionally, at least one promoter metal on a monolith support, the synthesis or regeneration comprising contacting the front face of a monolith support with at least one Group 8B metal compound and, optionally, at least one promoter metal compound in situ under ignition or autothermal process conditions.

2. The process of claim 1 wherein a solution containing the Group 8B metal compound and, optionally, the promoter metal compound is dripped or sprayed onto the front face of the monolith.

3. The process of claim 1 wherein the Group 8B metal is a platinum group metal.

4. The process of claim 3 wherein the platinum group metal is platinum.

5. The process of claim 1 wherein the promoter metal is selected from the group consisting of Groups 2A, 1B, 3A, 4A, the rare earth lanthanide elements, and mixtures thereof.

6. The process of claim 1 wherein the promoter metal is selected from the group consisting of tin and copper.

* * * * *